United States Patent [19]

Maas

[11] 4,002,456

[45] Jan. 11, 1977

[54] PLANT-GROWTH PROMOTING AGENT WHICH IS PROVIDED WITH TRACE ELEMENTS AND WHICH IS SUITED FOR USE IN ULTRA-LOW-VOLUME APPLICATIONS

[75] Inventor: Willem Maas, Weesp, Netherlands

[73] Assignee: U.S. Philips Corporation, New York, N.Y.

[22] Filed: Mar. 3, 1975

[21] Appl. No.: 554,970

[30] Foreign Application Priority Data

Mar. 8, 1974 Netherlands .................... 7403129

[52] U.S. Cl. .................................... 71/3; 71/27; 71/64 C; 71/118

[51] Int. Cl.$^2$ .................................... C05G 3/00

[58] Field of Search ............... 71/1, 11, 24, 25, 95, 71/3, 118, 27, 64 C

[56] References Cited

UNITED STATES PATENTS

| | | | |
|---|---|---|---|
| 3,551,134 | 12/1970 | Brenteson | 71/118 |
| 3,661,550 | 5/1972 | Downer et al. | 71/27 |

OTHER PUBLICATIONS

Chem. Abstracts, vol. 75, 1971, p. 351, 109261k, Halliday.

Primary Examiner—Charles N. Hart
Assistant Examiner—Ferris H. Lander
Attorney, Agent, or Firm—Frank R. Trifari; Norman N. Spain

[57] ABSTRACT

The invention relates to agents for plant-growth promotion which comprise trace elements and which are suited for ultra-low-volume application. The preparations comprise a solution of the chloride of the trace elements and/or boric acid in N-methylpyrrolidon. Furthermore, formamide or acetamide is dissolved in the agent as a nitrogen source. At option, the agent may contain a pesticide or pesticidal preparation, hexylene glycol, isophorone or a vegetable or animal wax or waxy product.

8 Claims, No Drawings

PLANT-GROWTH PROMOTING AGENT WHICH IS PROVIDED WITH TRACE ELEMENTS AND WHICH IS SUITED FOR USE IN ULTRA-LOW-VOLUME APPLICATIONS

The invention relates to plant-growth promoting agents which contain one or more trace elements as well as a nitrogen source.

Most trace elements such as Fe, Mn, Ni, Co, Zn are employed in the form of sulphates, chelates and also polyphosphates (Kirk-Othmer Encyclopedia of Chemical Technology, Second Edition, Vol. 9, p. 145-147). The element borine is usually applied as borate and molybdenum as molybdate.

For practical use said compounds of trace elements, also called micro-nutrients, may be distributed over the soil as such or may be sprayed over the soil and/or plants in the form of an aqueous solution. To promote the intake of micronutrients by the plant it is desirable to administer the micronutrients together with a nitrogen source such as for example urea, acetamide or formamide (Agricultural Chemicals, 24, No. 1, p. 52, 1969).

The micronutrients may be combined with solid or liquid fertilizers, which in general already contain a nitrogen source, to be distributed over the area to be treated after dilution with water. It has also been proposed to include the micronutrients in aqueous pesticidal spraying liquids (Agricultural Chemicals 24, No. 5, p. 23-31, 1969).

To obtain good results the aqueous solution of micronutrients, combined or not combined with fertilizer or pesticide, is to be sprayed over the aerea to be treated in comparatively large quantities. Usual quantities are for example 100-2000 liters per hectare.

A so-called "ultra-low-volume" application, in which quantities of 0.5-10 liters per hectare are employed, is not possible with the known micronutrient preparations. Treatment of large areas with aqueous solutions of micronutrients is consequently a very expensive and time-consuming procedure, which in many cases is uneconomic.

In the field of pesticides the "ultra-low-volume" concept is known. In recent years much interest has been aroused for spraying comparatively large areas of plants with small volumes of a liquid pesticidal preparation. The application in which per hectare 0.5-10 liters of a liquid pesticide is used is known by the name "ultra-low-volume" or abbreviated "U.L.V." application. Such low volumes of liquid are generally sprayed from an airplane. However, ground equipment for U.L.V. application is also available. For said U.L.V. applications special pesticidal preparations have been developed, which comprise a solution of a pesticidal compound in a solvent which is suited for U.L.V. application. Known solvents which are suitable for this purpose are alkylated aromatic hydrocarbons such as dodecylbenzene, high-aromatic naphts as well as isophorone, dimethylformamide and hexamethyl phosphoric acid triamide. In a single case a liquid pesticidal compound such as malathion is suitable as such for U.L.V. application. The U.L.V. pesticidal preparations may also comprise auxiliary substances such as phytotoxicity reducing substances. According to the Applicant's British Patent Specification 1,294,481 vegetable and animal waxes and derivatives thereof such as wool fat, wool fat alcohol and wool fat acid may be used for this purpose.

The known aqueous solutions of micronutrients, as previously stated, are not suited for U.L.V. application. Moreover, said preparations as well as the micronutrients themselves cannot be combined with the U.L.V. pesticidal liquids described above.

The Applicant has developed a plant-growth promoting agent containing trace elements which is suitable for U.L.V. use and which can moreover be combined with the U.L.V. pesticidal liquids.

More specifically, the present invention relates to a plant growth promoting agent which is provided with trace elements and a nitrogen source and is characterized in that the agent contains a solution of the chloride of one or more trace elements and/or boric acid in N-methylpyrrolidon, which solution also contains formamide or acetamide.

The specified ingredients all dissolve well in N-methylpyrrolidon. The solubilities of the chlorides of the trace elements Fe, Mn, Co, Zn, Cu, Mg, Ca vary from 5-50 grammes per 100 ml of solvent at a temperature of 20° C. The solubility of boric acid at 20° C is 20 grammes per 100 ml of N-methylpyrrolidon. Acetamide and formamide also dissolve well. For example, the solubility at 20° C of acetamide in N-methylpyrrolidon is 40 g per 100 ml. It is to be noted that if the agent according to the invention contains $CuCl_2$, the use of formamide is less suitable because of the resulting reduction of $Cu^{++}$ to $Cu^+$, which gives rise to precipitation. In such a case acetamide is to be used.

In a favourable embodiment the agent according to the invention also contains isophorone. It has been found that by the addition of isophorone, which mixes well with N-methylpyrrolidon, the favourable properties of the agent according to the invention are retained. Since isophorone is substantially cheaper than N-methylpyrrolidon, the addition of isophorone has the advantage that the agent according to the invention becomes cheaper. The amount of isophorone which may be contained in the agent according to the invention depends on the nature of the trace element compound or compounds used. Generally, the agent according to the invention contains max. 50 percent by volume of isophorone. Larger quantities are possible if the trace-element compoun(s) dissolve(s) well in isophorone. Such a well-soluble compound is $FeCl_3$, which at 20° C has a solubility in isophorone of 10 g of $FeCl_3$ per 100 ml of isophorone.

A further favourable embodiment of the agent according to the invention contains hexyleneglycol. Research conducted by the Applicant has revealed that the agent according to the invention as described in the preceding paragraphs, mixes less well with certain U.L.V. pesticidal preparations, viz. with those preparations in which an alkylated aromatic hydrocarbon such as for example dodecylbenzene is used as a solvent. Said less satisfactory miscibility is mainly caused by the presence of formamide or acetamide in the agent according to the invention. The trace elements present in the agent according to the invention also contribute to said less satisfactory miscibility. However, it has been found that said drawback does not occur if hexylene glycol is added to the agent according to the invention. The amount of hexylene glycol in the agent according to the invention is not bound to narrow limits. Good results are obtained i.e. a good miscibility also with U.L.V. preparations on an alkylated aromatic hydrocarbon basis, if the part by weight of hexylene glycol is approximately three times the part by weight of formamide or acetamide present in the agent.

Futhermore, a vegetable or animal wax or a waxy product hydrolized from wax may be dissolved in the inventive agent. The presence of a wax or waxy product reduces the possible phytotoxicity of the agent to the invention. If phytotoxic constituents are present such as for example isophorone or if the agent is combined with U.L.V. pesticidal liquids which contain such constituents, the addition of a wax or waxy product is very useful. Generally, the amount of wax or waxy product will vary from 0 to 25 g per 100 ml of final product. Suitable waxes and waxy products are inter alia carnauba wax, candelilla wax, flax wax, beeswax, but especially wool fat, wool fat alcohols and wool fat acids.

The composition of the agent according to the invention varies in accordance with the number and the amount of trace elements required for a specific application. Furthermore, it may be of importance for economic reasons to incorporate isophorone in the agent, in view of which a wax or waxy product is preferably added. In the case of mixing with pesticidal preparations which contain an alkylated aromatic hydrocarbon, it is desirable that the agent according to the invention comprises hexylene glycol. A highly active agent according to the invention which is useful in many circumstances comprises per 100 ml of final volume 5–40 g of the chloride of one or more trace elements and/or boric acid, 1–15 g of acetamide or formamide, 0–40 g of hexylene glycol and 0–5 g of wool fat alcohols dissolved in N-methylpyrrolidon or a mixture of N-methylpyrrolidon and isophorone.

Further details with respect to the precise composition of such favourable agents according to the invention are given in the examples at the end of the description.

The invention furthermore relates to agents as described hereinbefore which also include a liquid pesticide or a solution of a pesticide in a solvent which is suited for U.L.V. application. Suitable solvents are the previously mentioned alkylated aromatic hydrocarbons, isophorone, dimethylformamide, hexamethyl phosphoric acid triamide or mixtures thereof. In said agents according to the invention a pesticidal liquid or solution is combined with the solution of trace element compounds which have been described comprehensively hereinbefore. The resulting product is also a solution and has the advantage that when it is used both trace elements and a pesticide can be distributed over the area or plants to be treated in a single operation. The quantity of pesticidal liquid which in the agent according to the invention is combined with the trace element solution is 1–10 liters of the pesticidal liquid per 1–4 liters of the trace element solution, i.e. a mixing ratio which varies from 1:4 to 10:1. The amount of pesticidal compound in the combined agent according to the invention is roughly 100–500 grammes per liter of final solution.

As pesticidal compounds both a fungicidal, acaricidal, insecticidal or herbicidal substance may be used.

Especially combination agents which comprise an insecticidal or acaricidal compound are of great practical significance.

Suitable insecticidal substances are, inter alia insecticides based on chlorinated hydrocarbons such as D.D.T., endrin, endosulphan, dieldrin, telodrin, toxaphene, heptachlorine, strobane, lindane, on an organophosphor basis, for example malathion, naled, parathion dimethylparathion, phenotrothion, dichlorves, bromofos, azinfosmethyl, monocrotofos, metasystox, systox, disyston, trithion, E.P.N., diazinon, dimethoate, mevinfos, dipterex, ethion, fosfamidon, furthermore carbamates such as carbaryl, dimetilan and carbofuran. Examples of suitable acaricides are tetradifon, tetrasul, keltane, chloroparacide, fenson, chlorofenson and binapacryl.

The agents according to the invention can be prepared in a simple manner by dissolving the ingradients such as trace-element compound, formamide or acetamide, as the case may be a wax, waxy product and hexylene glycol, in N-methyl pyrrolidon or a mixture of N-methylpyrrolidon and isophorone. For the preparation of the combination agents a liquid pesticide or a solution of a pesticide may then also be dissolved in the resulting product.

The dosage suited for application of the agents according to the invention depends inter alia on the composition of the agent, the condition of the crop and climatological conditions. A dosage of 0.5–10 liters per hectare will generally yield satisfactory results.

The invention will be explained in more detail with reference to the following examples.

EXAMPLES

I. Composition of some agents according to the invention
which do not contain pesticidal compounds:
  a. 100 g/l $H_3BO_3$
     85 g/l acetamide
     250 g/l hexylene glycol
     ad 1000 ml of N-methylpyrrolidon.
  b. 50 g/l $FeCl_3.6H_2O$
     22 g/l $MnCl_3.4H_2O$
     17 g/l $H_3BO_3$
     11 g/l $CuCl_2.2H_2O$
     5 g/l $ZnCl_2$
     4 g/l $NiCl_2.6H_2O$
     0.8 g/l $CoCl_2.6H_2O$
     8 g/l $MgCl_2.6H_2O$
     11 g/l $CaCl_2.2H_2O$
     81 g/l acetamide
     250 g/l hexylene glycol
     ad 1000 ml of N-methylpyrrolidon
  c. 200 g/l $FeCl_3.H_2O$
     10 g/l wool fat alcohols
     80 g/l acetamide 250 g/l hexylene glycol 236 g/l isophorone
     ad 1000 ml of N-methylpyrrolidon
  d. 100 g/l $ZnCl_2$
     65 g/l formamide
     300 g/l hexylene glycol
     ad 1000 ml of N-methylpyrrolidon
  e. 50 g/l $FeCl_3.6H_2O$
     20 g/l $MnCl_2.4H_2O$
     20 g/l $H_3BO_3$
     17 g/l $CuCl_2.2H_2O$
     5 g/l $ZnCl_2$
     4 g/l $NiCl_2.6H_2O$
     1 g/l $CoCl_2.6H_2O$
     85 g/l acetamide
     250 g/l hexylene glycol
     20 g/l wool fat alcohols
     ad 1000 ml of (1:1) mixture of N-methylpyrrolidon and
     isophorone.

II. Composition of some agents according to the invention which contain a pesticidal compound:

a. 300 g/l DDT
25 g/l $FeCl_3.6H_2O$
10 g/l $MnCl_2.4H_2O$
10 g/l $H_3BO_3$
9 g/l $CuCl_2.2H_2O$
2 g/l $ZnCl_2$
40 g/l acetamide
120 g/l hexylene glycol
20 g/l wool fat alcohols
ad 1000 ml of (1:1) mixture of N-methylpyrrolidon and isophone b. 100 g/l tetradifon
50 g/l $FeCl_3.6H_2O$
40 g/l acetamide
120 g/l hexylene glycol
20 g/l wool fat alcohols
ad 1000 ml (1:3) mixture of N-methylpyrrolidon and isophorone.

What is claimed is:

1. A plant growth promoting composition particularly adapted for use in U.L.V. applications, said composition comprising a solution in a solvent comprising N-methylpyrrolidene of 5–40 g per 100 ml of at least 1 micronutrient selected from the group consisting of the chlorides of the trace elements and boric acid and 1–15 g per 100 ml of a nitrogen source selected from the group consisting of acetamide and formamide.

2. The plant growth promoting composition of claim 1 wherein up to about 50% by volume of the N-methylpyroolidene is replaced by isophorone.

3. The plant growth promoting composition of claim 2 wherein 0–40 g per 100 ml of hexylene glycol is present.

4. The plant growth promoting composition of claim 3 wherein in addition up to 5 g per 100 ml of a waxy material selected from the group consisting of vegetable wax, animal wax and waxy hydrolysis products thereof is present.

5. The plant growth promoting composition of claim 4 wherein the waxy material is wool fat alcohol.

6. The plant growth promoting composition of claim 1 wherein in addition a liquid pesticide composition suitable for ULV application is present.

7. The plant growth promoting composition of claim 6 wherein the liquid pesticide composition contains a solvent selected from the group consisting of alkylated aromatic hydrocarbons, isophorone, dimethylformamide, hexamethyl phosphoric acid triamide and mixtures thereof.

8. A method of promoting plant growth, characterized in that an agent as claimed in claim 1 is sprayed over the area to be treated in a dosage of 0.5–10 liters per hectare.

* * * * *

UNITED STATES PATENT AND TRADEMARK OFFICE
CERTIFICATE OF CORRECTION

PATENT NO. : 4,002,456
DATED : January 11, 1977
INVENTOR(S) : WILLEM MAAS

It is certified that error appears in the above-identified patent and that said Letters Patent are hereby corrected as shown below:

Col. 3, line 6, change "to" to -- of --.

Col. 6, line 26, change "an agent" to -- a composition --.

Signed and Sealed this twelfth Day of July 1977

[SEAL]

Attest:

RUTH C. MASON
Attesting Officer

C. MARSHALL DANN
Commissioner of Patents and Trademarks